United States Patent [19]

Miki et al.

[11] 4,297,357
[45] Oct. 27, 1981

[54] N-PHENETHYLACETAMIDE COMPOUNDS AND PROCESS FOR PREPARATION THEREOF

[75] Inventors: Tosaku Miki; Masahide Asano, both of Minamifunabori, Japan

[73] Assignee: Daiichi Seiyaku Co., Ltd., Tokyo, Japan

[21] Appl. No.: 70,085

[22] Filed: Aug. 27, 1979

[30] Foreign Application Priority Data

Aug. 25, 1978 [JP] Japan .................................. 53-103652
Jul. 25, 1979 [JP] Japan .................................. 54-94597

[51] Int. Cl.³ .................. A61K 31/505; A61K 31/44; A61K 31/165
[52] U.S. Cl. .................................. 424/251; 424/263; 424/324; 544/298; 544/319; 544/326; 544/330; 546/309; 560/21; 564/86; 564/157; 564/168
[58] Field of Search .................. 424/324, 263, 251; 260/558 R, 558 S, 558 P, 558 A; 564/168, 157, 86; 560/21; 546/309; 544/319, 326, 298, 330

[56] References Cited

U.S. PATENT DOCUMENTS 3,657,341  4/1972  Thorne .................................. 424/324

Primary Examiner—Frederick E. Waddell
Attorney, Agent, or Firm—Sughrue, Mion, Zinn, Macpeak & Seas

[57] ABSTRACT

N-phenethylacetamide compounds of the formula:

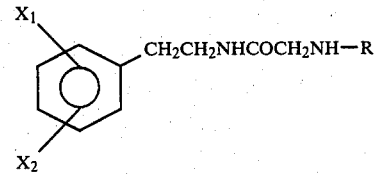

wherein $X_1$ represents a lower alkoxy group, $X_2$ represents a hydrogen atom or a lower alkoxy group and R represents a phenyl group, a pyridyl group, a pyrimidinyl group or a benzoyl group, each of which may have one or more substituents selected from a halogen atom, a carbamoyl group, a lower alkoxy group, a sulfamoyl group, an amino group, a lower alkylamino group, a lower alkylthio group, a hydroxy group and a lower alkoxycarbonyl group; the parmaceutically acceptable acid addition salts and hydrates thereof; as well as the process for preparing such compounds and salts and hydrates thereof; the compounds, their salts and their hydrates having a distinct anti-peptic ulcer activity in human and animals.

9 Claims, No Drawings

N-PHENETHYLACETAMIDE COMPOUNDS AND PROCESS FOR PREPARATION THEREOF

BACKGROUND OF THE INVENTION

1. Field of the Invention

This invention relates to N-phenethylacetamide compounds and to processes for preparing the same. More particularly, this invention relates to novel N-phenethylacetamide compounds represented by the formula (I):

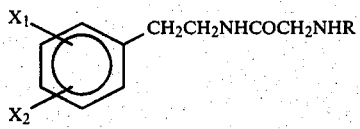

wherein $X_1$ represents a lower alkoxy group, $X_2$ represents a hydrogen atom or a lower alkoxy group and R represents a phenyl group, a pyridyl group, a pyrimidinyl group or a benzoyl group, each of which may have one or more substituents selected from a halogen atom, a carbamoyl group, a lower alkoxy group, a sulfamoyl group, an amino group, a lower alkylamino group, a lower alkylthio group, a hydroxy group and a lower alkoxycarbonyl group.

The invention also relates to hydrates (hydrated crystals containing three molecules of crystallized water) or salts of the compounds of the formula (I) and to the process for preparing such compounds, their salts and their hydrates.

The compounds having the formula (I) above as well as the pharmaceutically acceptable salts and hydrates thereof have distinctive and unique anti-peptic ulcer activity in human and animals.

2. Description of the Prior Art

Up to now, a compound somewhat structurally similar to those of this invention, 3,4-dihydroxyphenethylamine (abbreviated as Dopamine) is known and is described by L. S. Goodman and A. Gilman, *The Pharmacological Basis of Therapeutics*, (Fourth Edition), p. 234, 1970.

The compound, however, has not proved satisfactory for clinical use because of its undesirable side effects or insufficient activities as shown hereinafter.

SUMMARY OF THE INVENTION

Accordingly, an object of this invention is to provide compounds having the formula (I) above which have excellent anti-peptic ulcer properties and can be safely used clinically without deleterious side effects.

Another object is to provide a process for preparing such compounds and their hydrates or pharmaceutically acceptable salts.

Further object will be described hereinafter in detail.

DETAILED DESCRIPTION OF THE INVENTION

This invention provides N-phenethylacetamide compounds represented by the formula (I):

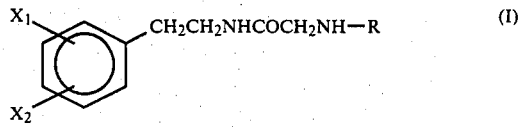

wherein $X_1$ represents a lower alkoxy group, $X_2$ represents a hydrogen atom or a lower alkoxy group and R represents a phenyl group, a pyridyl group, a pyrimidinyl group or a benzoyl group, each of which may have one or more substituents selected from a halogen atom, a carbamoyl group, a lower alkoxy group, a sulfamoyl group, an amino group, a lower alkylamino group, a lower alkylthio group, a hydroxy group and a lower alkoxycarbonyl group; the pharmaceutically acceptable acid addition salts and hydrates thereof; as well as a process for preparing such compounds, their salts and their hydrates.

The compounds of this invention can be prepared by one of the methods represented by the following reaction schematics:

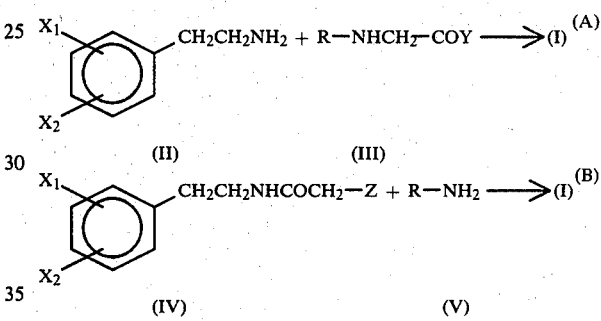

wherein —COY represents a carboxyl group or a functional group thereof such as an ester, a carboxylic anhydride or the like, Z represents a halogen atom and $X_1$, $X_2$ and R are the same as hereinbefore defined.

The term "lower" as used herein in describing the $X_1$, $X_2$ and R substituents designates a moiety having 1 to 6 carbon atoms.

The N-phenethylacetamide derivatives of this invention having the formula (I) can be prepared as follows.

Method A:

The compounds of this invention can be prepared by reacting a phenethylamine (II) with a carboxylic acid or a functional derivative thereof (III) in the presence or absence of a solvent.

More specifically, the reaction can be carried out by heating the phenethylamine (II) with the carboxylic acid or the lower alkyl ester thereof (III) at a temperature of about 110° C. to about 190° C. for about 1 to about 10 hours. When the substituent —COY in the compound (III) represents a carboxylic anhydride, the reaction can be carried out by reacting the phenethylamine (II) with the carboxylic anhydride (III) in a suitable solvent under cooling or at room temperature (e.g., 20° C.–30° C.) for about 1 to several hours. The most suitable solvent for this reaction is dimethylformamide. The reaction may be conducted advantageously in the presence of an acid-acceptor such as triethylamine and the like.

Further, the compound of this invention can be produced by heating the ammonium salt represented by the formula (VI):

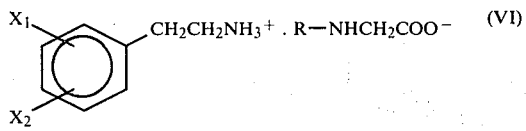

wherein $X_1$, $X_2$ and R are as defined above, at a temperature of about 110° C. to about 190° C. for about 1 to about 10 hours. The ammonium salt having the formula (VI) can be easily produced by mixing an equimolar amount of the compound (II) and the compound (III) at room temperature.

Method B:

The compounds of this invention can also be prepared by reacting the compound (VI) with the amine (V) in the presence or absence of a solvent.

When the amine (V) is used in an excess amount over the equimolar amount relative to the compound (IV) in this method, the reaction can be carried out by heating the compound (IV) and the amine (V) without any solvent at a temperature of about 140° C. to about 180° C. for about 1 to about 5 hours. When the amine (V) is used in an equimolar amount relative to the compound (IV) in this method, this reaction can be carried out by heating the compound (IV) and the amine (V) at a temperature of about 60° C. to about 100° C. for about 3 to about 5 hours in a suitable solvent in the presence of a suitable acid-acceptor. Examples of solvents which can be used in this reaction are inert solvents selected from hydrocarbon halides, ethers, benzenes, pyridines and dimethylformamide, preferably dimethylformamide. Examples of acid-acceptors are a carbonate, a hydroxide or an oxide of an alkali or alkaline earth metal.

The reaction can be advantageously carried out by adding an iodine compound such as sodium iodide, if desired, whereby the reaction proceeds smoothly and the desired compound can be obtained in high yield. The desired compound of this invention thus obtained can be isolated and purified by a conventional method such as extraction, chromatography, recrystallization and the like.

According to the process described above, the compound of this invention is normally obtained as a free base, but it can also be obtained as a pharmaceutically acceptable acid addition salt thereof, if necessary, according to the procedure well known in the art.

Of the starting materials, the compounds (III) are novel compounds and can be produced through known reactions, for example, by reacting an amine of the formula (V) with the compound having the formula (VII):

ZCH$_2$—COY          (VII)

wherein Z and —COY are as defined above, as shown by the examples described below.

Especially interesting examples of compounds of this invention are: 2-(3-carbamoylphenylamino)-N-(3,4-dimethoxyphenethyl)acetamide, 2-(2-carbamoyl-5-chlorophenylamino)-N-(3,4-dimethoxyphenethyl-)acetamide and 2-(phenylamino)-N-(3,4-dimethoxyphenethyl)acetamide.

In a further investigation of pharmaceutical preparation of the representative compound of the invention, 2-(3-carbamoylphenylamino)-N-(3,4-dimethoxyphenethyl)acetamide, it was found that the free base and/or the acid addition salt of this compound can be converted into a novel hydrated compound having three molecules of crystallized water by treating it with water.

More specifically, in order to prepare the hydrate, the free base and/or the acid addition salt is suspended or dissolved in water and stirred for about 10 minutes to about 20 hours to room temperature or at an elevated temperature below the boiling point of the suspension or solution and then allowed to stand at the same temperature or under cooling to precipitate the crystals of the hydrate. The resulting crystals are collected by filtration and air-dried at room temperature to obtain the desired hydrate. In dissolving the free base and/or the acid addition salt in water, a suitable hydrophilic solvent such as a lower alcohol, acetone, dioxane, etc., may be added to increase the solubility of the compounds.

The hydrated crystal of 2-(3-carbamoylphenylamino)-N-(3,4-dimethoxyphenethyl)acetamide thus obtained is a novel compound having three molecules of crystallized water and the presence of the crystallized water was confirmed by some analytical means such as elemental analysis, melting point, differential thermal analysis, infrared absorption spectrum, X-ray analysis, etc. The hydrate of this invention is especially useful in preparing a pharmaceutical composition containing one of the compounds of this invention since the hydrate of this invention possesses remarkably stable chemical and physical properties which are very important factors for producing pharmaceutical preparations such as capsules, tablets, powders, granules, etc. The stability of the hydrate of this invention was confirmed as follows.

That is, as a result of the measurement of isothermal absorption curve, it was confirmed that the hydrate of this invention was very stable under high humidity at an elevated temperature because it had not relative critical humidity. It was also confirmed by thin layer chromatography that the hydrate was stable in methanol at room temperature for 48 hours. This means that it is possible to use methanol as a solvent in producing pharmaceutical preparations. It was further confirmed that a mixture of the hydrate of this invention with various kinds of additives such as carriers, diluents, etc., was stable under accelerated conditions, i.e., under high humidity at an elevated temperature for one month or under the light irradiation from 2,500 lux for one month. The results of the stability of a mixture of the hydrate with a various kind of additives are shown in Table 1.

TABLE 1

| Stability of Mixture of Hydrate with Various Kinds of Additives (one month storage) | | | |
|---|---|---|---|
| Sample | | Hydrate of This Invention | |
| Additives | Conditions | at 40° C., 75% Relative Humidity | 2500 lux |
| Lactose | | — | — |
| Sucrose | | — | — |
| Cornstarch | | — | — |
| Mannitol | | — | — |
| Calcium Phosphate Dibasic | | — | — |
| Crystalline Cellulose | | — | — |
| Hydroxypropylcellulose | | — | — |
| Hydroxypropylmethylcellulose | | ± | — |
| Magnesium Stearate | | — | — |
| Talc | | — | — |
| Macrogol 6000 | | — | — |

TABLE 1-continued

Stability of Mixture of Hydrate with Various Kinds of Additives (one month storage)

| Sample | | Hydrate of This Invention | |
|---|---|---|---|
| Additives | Conditions | at 40° C., 75% Relative Humidity | 2500 lux |
| Polyvinyl Alcohol | | — | — |

Note 1.
The meaning of the symbols is as follows.
—:no color change
±:slight color change
+:clear color change Note 2.
Samples were prepared by well mixing 100 mg of the hydrate with 100 mg of the additive except for magnesium stearate and talc. In case of using magnesium stearate or talc as the additive, 10 mg of the hydrate was used.

The compounds of the present invention have an excellent and characteristic anti-ulcer activity ordinarily not obtained from known typical agents.

To demonstrate the superiority of the present compounds, the pharmacological properties of several representative compounds of the present invention were compared with those of sulpiride [N-[(1-ethyl-2-pyrrolidinyl)methyl]-2-methoxy-5-sulfamoylbenzamide] which is one of the representative anti-ulcer agents. In this experiment, test compounds were administered as the free base, in the form of the hydrochloric acid salts or in the form of the hydrate.

As is apparent from Tables 2 to 4, N-phenethylacetamide derivatives of this invention are expected to show remarkable effect to gastric ulcers, especially to Stress Ulcer.

TABLE 2

Inhibitory Effect on Stress Ulcer in Rat (by intraperitoneal injection)

$$\underset{X_2}{\overset{X_1}{\bigcirc}}-CH_2CH_2NHCOCH_2NH-R$$

| $X_1$ | $X_2$ | R | Dose (mg/kg) | Inhibitory Effect (%) |
|---|---|---|---|---|
| 3-CH$_3$O— | 4-CH$_3$O— | 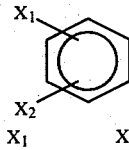 . HCl | 100 | 42** |
| " | " | 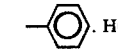 . HCl | " | 36* |
| " | " | 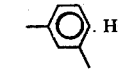 . HCl | " | 20* |
| " | " | 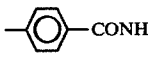 | " | 38** |
| " | " | 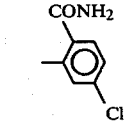 | " | 44* |
| " | " | 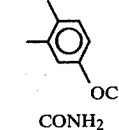 | " | 34* |
| " | " | 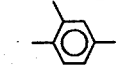 | " | 33* |
| " | " | 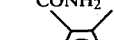 . HCl | " | 53** |
| " | " | 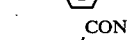 . 3H$_2$O | " | 52* |
| " | " | 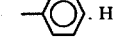 . HCl | " | 35 |
| " | " | 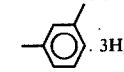 | " | 21* |

TABLE 2-continued

Inhibitory Effect on Stress Ulcer in Rat
(by intraperitoneal injection)

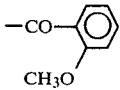

| $X_1$ | $X_2$ | R | Dose (mg/kg) | Inhibitory Effect (%) |
|---|---|---|---|---|
| " | " | 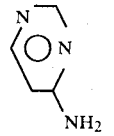 | " | 50** |
| " | " | 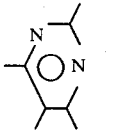 | " | 27* |
| " | " | 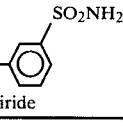 | " | 17* |
| " | " |  | " | 47* |
| | | Sulpiride | " | 27* |

TABLE 3

Inhibitory Effect on Stress Ulcer in Rat
(by oral administration)

| Compound | Inhibitory Effect (%) Dose (mg/kg) | | |
|---|---|---|---|
| | 100 | 200 | 400 |
| Compound 1 | 5 | 17** | 18* |
| Compound 2 | 5 | 21* | 33** |
| Compound 3 | 20 | 20 | 25* |
| Sulpiride | 5 | 4 | 11 |

TABLE 4

Inhibitory Effect on Stress Ulcer in Rat
(by oral administration)

| Compound | Inhibitory Effect (%) Dose (mg/kg) | | |
|---|---|---|---|
| | 100 | 200 | 400 |
| Compound 4 | 23 | 36 | 70** |
| Sulpiride | 29 | 20 | 39* |

Note 1.
*means "significantly different from control (p<0.05)".
**means "significantly different from control (p<0.01)".
Note 2. Inhibitory effect on Stress Ulcer was examined according to Water Immersion Restraint Method disclosed in *Japanese Journal of Pharmacology*, Vol. 18, 9 (1968).
Note 3. As test animals, seven rats weighing about 300 g were used for each dosage level.
Note 4. Test compounds were injected intraperitoneally or administered orally before 30 minutes of water immersion restrain.
Note 5. Test animals were immersed and restrained in water at 21° C. for 20 hours in experiment of Tables 2 and 3 and at 21° C. for 7 hours in experiment of Table 4.
Note 6. The compounds described in the above Tables and in Tables described hereinafter are as follows:
  Compound 1: 2-(2-carbamoyl-5-chlorophenylamino)-N-(3,4-dimethoxyphenethyl)acetamide
  Compound 2: 2-(3-carbamoylphenylamino)-N-(3,4-dimethoxyphenethyl)acetamide hydrochloride
  Compound 3: 2-(phenylamino)-N-(3,4-dimethoxyphenethyl)acetamide hydrochloride
  Compound 4: 2-(3-carbamoylphenylamino)-N-(3,4-dimethoxyphenethyl)acetamide.3H$_2$O Further, the compounds of this invention exhibit a characteristic anti-ulcer action. That is, the superior anti-ulcer effect of the compounds of this invention is due to central action in origin, whereas that of almost all of conventional anti-ulcer agents is due to peripheral action. Accordingly, the compounds of this invention are very useful as a unique type of anti-ulcer agent. The central action of the compounds of this invention has been confirmed by the experiment of inhibitory effect on the secretion of gastric acids in rats, using a modification of "Shield's Method" described in *British Journal of Pharmacology*, Vol. 13, 54 (1958). In this experiment, the compounds of this invention remarkably inhibited centrally mediated secretion of gastric acids induced by administration of insulin. On the other hand, the compounds of this invention did not inhibit secretion of gastric acids induced by administration of carpronium chloride which acts locally on the stomach. The results obtained in this experiment are shown in Table 5 and Table 6 below.

TABLE 5

Inhibitory Effects on Secretion of Gastric Acids Induced by Insuline (dose: 4 ug/kg, i.v.)

| Compound | Dose (mg/kg, i.v.) | Inhibition (%) |
|---|---|---|
| Compound 1 | 50 | 50 |
| Compound 2 | 10 | 80 |

TABLE 6

Inhibitory Effects on Secretion of Gastric Acids Induced by Carponium Chloride (dose: 8–10 μg/rat, i.v.)

| Compound | Dose (mg/kg, i.v.) | Inhibition (%) |
|---|---|---|
| Compound 1 | 50 | 0 |
| Compound 2 | 50 | 0 |
| Compound 2 | 100 | 0 |

As set forth previously, it is known that Dopamine, which is somewhat structurally similar to those of this invention, has anti-ulcer activity. [*The Pharmacological Basis of Therapeutics*, 4th Edition, 234 (1970)]. However, it is apparent that the anti-ulcer activity of Dopamine is not due to its central action because it cannot cross blood brain barrier. Therefore, the mechanism of the anti-ulcer activity of Dopamine is essentially different from that of the compounds of this invention. Further, it is well known that Dopamine acts strongly on cardiovascular system and has been employed in the treatment of shock syndromes [*Pharmacometrics*, Vol. 8, 835–846 (1974)]. Accordingly, use of Dopamine for the treatment of peptic ulcer is not appropriate.

The compounds of this invention have been found to have a low acute toxicity over 2 g/kg body weight ($LD_{50}$) in mice when orally administered. Therefore, the compounds of this invention are extremely low toxic and satisfactory for an anti-ulcer agent for human and animals.

When the compounds of this invention are administered, they can be formulated into any desired pharmaceutical dosage forms which can be prepared by conventional techniques such as capsules, tablets, powders, injections or suppositories.

A suitable dosage amount administered can range from about 50 to 450 mg/day for adult human in single or multiple doses along with appropriate pharmaceutically acceptable carriers and diluents such as lactose, sucrose, sorbitol, starch, gelatin, magnesium stearate, polyethylene glycol, etc.

The present invention is further illustrated by the following Examples. Unless otherwise indicated, all percents, ratios and parts are by weight.

EXAMPLE 1

To a mixture of 7.73 g of 2-chloro-N-(3,4-dimetoxyphenethyl)acetamide, 5.12 g of 2-amino-4-chlorobenzamide, 13.5 g of sodium iodide and 3.63 g of magnesium oxide was added 30 ml of dimethylformamide and the resulting mixture was stirred at 90° to 100° C. for 4.5 hours. The reaction solution was concentrated under reduced pressure and the residue was extracted with 500 ml of chloroform. The chloroform extract was washed successively with 10% hydrochloric acid, water, a 5% aqueous sodium carbonate solution, a 5% aqueous sodium sulfite solution and water, dried and then concentrated to dryness under reduced pressure. The residue was recrystallized from methanol to obtain 8.01 g of 2-(2-carbamoyl-5-chlorophenylamino)-N-(3,4-dimethoxyphenethyl)acetamide having a melting point of 167.5°–168.5° C.

Elemental Analysis for $C_{19}H_{22}O_4N_3Cl$: Calcd. (%): C, 58.24; H, 5.66; N, 10.72. Found (%): C, 58.26; H, 5.59; N, 10.70.

EXAMPLE 2

To 0.36 g of 3,4-dimethoxyphenethylamine was added 0.46 g of N-(2-carbamoyl-5-chlorophenyl)glycine and the mixture was stirred at 175° to 185° C. for 6 hours under nitrogen atmosphere. After cooling, the mixture was dissolved in 50 ml of chloroform and the chloroform solution was filtered to remove insoluble materials. The filtrate was washed with 5% hydrochloric acid, a 5% aqueous sodium carbonate solution and water and then dried. The solvent was evaporated in vacuo, and the residue was subjected to column chromatography on silica gel (15 g) and eluted with a mixture of chloroform and methanol (50:1 by volume). The eluate was concentrated to give 0.44 g of 2-(2-carbamoyl-5-chlorophenylamino)-N-(3,4-dimethoxyphenethyl)acetamide as colorless needles having a melting point of 167.5°–169° C.

EXAMPLE 3

2.3 g of N-(2-carbamoyl-5-chlorophenyl)glycine was dissolved in 600 ml of ethyl acetate while stirring and then a solution of 1.8 g of 3,4-dimethoxyphenethylamine dissolved in 20 ml of ethyl acetate was added dropwise thereto while stirring to form 3,4-dimethoxyphenethylamine.N-(2-carbamoyl-5-chlorophenyl)glycine salt as crystals. The crystals were collected by filtration and dried to obtain 3.9 g of the salt having a melting point of 181°–185° C.

Elemental Analysis for $C_{19}H_{24}O_5N_3Cl$: Calcd. (%): C, 55.68; H, 5.90; N, 10.25. Found (%): C, 55.70; H, 5.92; N, 10.26.

Under nitrogen atmosphere, 2.0 g of the salt was melted at 190° to 200° C. over a period of 1 hour. After cooling, the resulting mixture was dissolved in 100 ml of chloroform. After filtration of insoluble materials, the filtrate was washed with 5% hydrochloric acid, a 5% aqueous sodium carbonate solution and water and then dried. The solvent was evaporated in vacuo, and the residue was subjected to column chromatography on silica gel (30 g) and eluted with a mixture of chloroform and methanol (50:1 by volume). The eluate was concentrated to give crude crystals of 2-(2-carbamoyl-5-chlorophenylamino)-N-(3,4-dimethoxyphenethyl)acetamide. The crude crystals thus obtained were recrystallized from a mixture of methanol and diethyl ether to obtain 1.2 g of pure crystals having a melting point of 167°–168° C.

EXAMPLE 4

A mixture of 3.6 g of 3,4-dimetoxyphenethylamine and 4.2 g of N-(3-carbamoylphenyl)glycine methyl ester was melted at 110° to 120° C. under nitrogen atmosphere and allowed to stand at the same temperature for 6 hours. After cooling, the reaction mixture was dissolved in methanol and 20 ml of methanol containing 5% hydrogen chloride by weight was added. The resulting mixture was concentrated to dryness under reduced pressure, and the residue was recrystallized from a mixture of methanol and diethyl ether to obtain 5.0 g of 2-(3-carbamoylphenylamino)-N-(3,4-dimethoxyphenyl)acetamide hydrochloride having a melting point of 140°–155° C. (dec.).

Elemental Analysis for $C_{19}H_{24}O_4n_3Cl$: Calcd. (%): C, 57.94; H, 6.14; N, 10.67. Found (%): C, 57.64; H, 6.08; N, 10.77.

To 3.0 g of 2-(3-carbamoylphenylamino)-N-(3,4-dimethoxyphenethyl)acetamide hydrochloride were added 20 ml of a 5% aqueous sodium carbonate solution and 125 ml of chloroform, and the mixture was stirred at room temperature until the crystals of the above hydrochloride was completely dissolved. The chloroform layer was separated, washed with water, dried and the solvent was evaporated to dryness in vacuo. The residue was recrystallized from a mixture of methanol and diethyl ether to obtain 2.3 g of 2-(3-carbamoylphenylamino)-N-(3,4-dimethoxyphenethyl)acetamide having a melting point of 133°-135° C.

Elemental Analysis for $C_{19}H_{23}O_4N_3$: Calcd. (%): C, 63.85; H, 6.48; N, 11.76. Found (%): C, 63.59; H, 6.40; N, 11.71.

EXAMPLE 5

To a solution 5.0 g of N-(3-carbamoylphenyl)glycine dissolved in 65 ml of tetrahydrofuran was added dropwise a mixture solution of 2.3 ml of trichloromethyl chloroformate and 10 ml of tetrahydrofuran under refluxing. After the refluxing was continued for an additional 3 hours, the reaction solution was concentrated under reduced pressure and 30 ml of petroleum ether was added dropwise while stirring under cooling. The precipitate was collected by filtration, washed with petroleum ether and dried to obtain 5.3 g of N-(3-carbamoylphenyl)-N-carboxyglycine anhydride as colorless crystals having a melting point of 160°-171° C. (dec.). 5.3 g of the compound thus obtained was added in small portions to a mixture of 4.4 g of 3,4-dimethoxyphenethylamine, 4.9 g of triethylamine and 30 ml of dimethylformamide under ice-cooling. After completion of addition, the reaction solution was allowed to warm gradually to room temperature and stirred for 1.5 hours. The reaction solution was at first acidified with 25 ml of 10% hydrochloric acid and subsequently rendered alkaline with 5.3 g of sodium carbonate again. The alkaline solution was concentrated under reduced pressure. The residue was dissolved in 70 ml of chloroform, washed with a small amount of water, dried and the solvent was then evaporated to dryness in vacuo. The residue was subjected to column chromatography on silica gel (40 g) and eluted with a mixture of chloroform and methanol (100:1 by volume). The eluate was concentrated to obtain 2-(3-carbamoylphenylamino)-N-(3,4-dimethoxyphenethyl)acetamide. The free base was converted into the corresponding hydrochloride salt by reacting the free base with a 5% methanolic solution of hydrogen chloride as described in Example 4. The salt was recrystallized from a mixture of methanol and diethyl ether to obtain 3.1 g of 2-(3-carbamoylphenylamino)-N-(3,4-dimethoxyphenethyl)acetamide hydrochloride having a melting point of 140°-155° C. (dec.).

EXAMPLE 6

100 ml of dimethylformamide was added to a mixture of 25.8 g of 2-chloro-N-(3,4-dimetoxyphenethyl)acetamide, 13.6 g of m-aminobenzamide, 15.0 g of sodium iodide and 20.0 g of calcium carbonate, and the mixture was stirred at 60° C. for 4 hours. The same procedure as described in Example 1 was followed to obtain 2-(3-carbamoylphenylamino)-N-(3,4-dimethoxyphenethyl)acetamide. The product was converted to the corresponding hydrochloride salt as described in Example 5. The salt was recrystallized from a mixture of methanol and diethyl ether to obtain 21.7 g of 2-(3-carbamoylphenylamino)-N-(3,4-dimethoxyphenethyl)acetamide hydrochloride having a melting point of 142°-155° C. (dec.).

EXAMPLE 7

To a solution of 1.0 g of 2-(3-carbamoylphenylamino)-N-(3,4-dimethoxyphenethyl)acetamide dissolved in 50 ml of ethanol was added a solution of 0.96 g of picric acid dissolved in 20 ml of ethanol. The mixture was moderately concentrated under reduced pressure and allowed to stand to obtain 1.0 g of the picrate having a melting point of 115°-120° C. (dec.).

Elemental Analysis for $C_{25}H_{26}O_{11}N_6$: Calcd. (%): C, 51.20; H, 4.47; N, 14.33. Found (%): C, 51.34; H, 4.51; N, 14.63.

EXAMPLES 8 TO 35

By repeating substantially the same procedures as described in one of the Examples 1 to 6, various other N-phenethylamine derivatives were prepared. The results obtained are summarized in Table 7 below.

TABLE 7

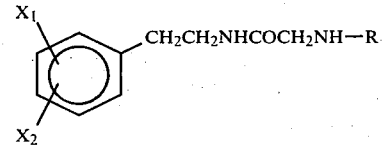

| Ex. No. | $X_1$ | $X_2$ | R | M.P. (°C.) | Calculated / Found C | H | N |
|---|---|---|---|---|---|---|---|
| 8 | 3-CH₃O— | 4-CH₃O— | —⟨○⟩·HCl | 160–170 (dec.) | 61.62 / 61.68 | 6.61 / 6.58 | 7.98 / 7.92 |
| 9 | " | " | —⟨○⟩·HCl (Cl) | 140–160 (dec.) | 56.11 / 56.45 | 5.76 / 5.80 | 7.27 / 7.40 |
| 10 | " | " | —⟨○⟩—Cl·HCl | 155–165 (dec.) | 56.11 / 56.25 | 5.76 / 5.72 | 7.27 / 7.25 |

TABLE 7-continued $$\text{X}_1, \text{X}_2\text{-C}_6\text{H}_3\text{-CH}_2\text{CH}_2\text{NHCOCH}_2\text{NH}-R$$

| Ex. No. | X₁ | X₂ | R | M.P. (°C.) | Analysis (%) Calculated / Found | | |
|---|---|---|---|---|---|---|---|
| | | | | | C | H | N |
| 11 | " | " | 2-Cl-C₆H₄ | 68–70 | 61.98 / 61.78 | 6.07 / 6.07 | 8.03 / 8.03 |
| 12 | " | " | 4-OCH₃-C₆H₄ · HCl | 140–163 (dec.) | 59.92 / 59.67 | 6.62 / 6.71 | 7.36 / 7.63 |
| 13 | " | " | —CO-(2-OCH₃)C₆H₄ | 125–127 | 64.50 / 64.64 | 6.50 / 6.40 | 7.52 / 7.49 |
| 14 | " | " | —CO-(3-OCH₃)C₆H₄ | 118–120 | 64.50 / 64.40 | 6.50 / 6.49 | 7.52 / 7.43 |
| 15 | " | " | 4-CONH₂-C₆H₄ · HCl | 155–165 (dec.) | 57.94 / 57.78 | 6.14 / 6.21 | 10.67 / 10.61 |
| 16 | " | " | 3-Cl-4-CONH₂-C₆H₃ · HCl | 175–184 (dec.) | 53.28 / 53.61 | 5.41 / 5.42 | 9.81 / 9.82 |
| 17 | " | " | 3-Cl-4-OCH₃-5-CONH₂-C₆H₂ | 206–207.5 | 56.94 / 56.76 | 5.73 / 5.76 | 9.96 / 10.00 |
| 18 | " | " | 2-CONH₂-C₆H₄ | 149–151 | 63.85 / 63.61 | 6.48 / 6.52 | 11.76 / 11.60 |
| 19 | " | " | 2-COOC₂H₅-4-Cl-C₆H₃ | 141–142 | 59.93 / 60.06 | 5.99 / 6.10 | 6.66 / 6.82 |
| 20 | " | " | 2-CONH₂-4-OCH₃-C₆H₃ | 151–152 | 62.00 / 61.79 | 6.50 / 6.52 | 10.85 / 11.12 |
| 21 | " | " | 2-CONH₂-4-Cl-C₆H₃ | 169–169.5 | 58.24 / 58.18 | 5.66 / 5.55 | 10.72 / 10.67 |
| 22 | " | " | 2-CONH₂-5-OCH₃-C₆H₃ | 104–107 | 62.00 / 61.86 | 6.50 / 6.30 | 10.85 / 10.80 |
| 23 | " | " | 2-CONH₂-6-Cl-C₆H₃ | 170.5–171.5 | 58.24 / 58.35 | 5.66 / 5.66 | 10.72 / 10.73 |
| 24 | " | " | 2-CONH₂-3-Cl-C₆H₃ · HCl | 147–162 (dec.) | 53.28 / 53.27 | 5.41 / 5.50 | 9.81 / 9.80 |

TABLE 7-continued $$X_1\text{-}C_6H_3(X_2)\text{-}CH_2CH_2NHCOCH_2NH\text{-}R$$

| Ex. No. | $X_1$ | $X_2$ | R | M.P. (°C.) | Analysis (%) Calculated / Found | | |
|---|---|---|---|---|---|---|---|
| | | | | | C | H | N |
| 25 | " | " | 4-Cl-3-methyl-C₆H₃-CONH₂ | 165.5–167.5 | 58.23 / 58.05 | 5.66 / 5.63 | 10.72 / 10.52 |
| 26 | " | " | 3-methyl-C₆H₄-COOCH₃ | 118–119 | 64.50 / 64.73 | 6.50 / 6.56 | 7.52 / 7.37 |
| 27 | " | " | 4-Cl-3-methyl-C₆H₃-SO₂NH₂ | 170–171 | 50.52 / 51.14 | 5.18 / 5.20 | 9.82 / 9.63 |
| 28 | " | " | 3-methyl-C₆H₄-SO₂NH₂ | 140–141 | 54.95 / 54.92 | 5.89 / 6.10 | 10.68 / 10.18 |
| 29 | " | " | pyridyl-CH₂- | 97–98 | 64.74 / 64.67 | 6.71 / 6.75 | 13.33 / 13.41 |
| 30 | " | " | 4-NH₂-pyrimidinyl-CH₂- | 194.5–195.5 | 57.99 / 57.70 | 6.39 / 6.48 | 21.14 / 21.03 |
| 31 | " | " | 4-NHCH₃-5-Cl-6-CH₃S-pyrimidinyl-CH₂- | 175~7–184~5 | 50.76 / 50.78 | 5.68 / 5.66 | 16.44 / 16.87 |
| 32 | " | " | 4-OCH₃-pyrimidinyl-CH₂- | 155–156 | 58.94 / 58.94 | 6.40 / 6.39 | 16.18 / 16.13 |
| 33 | " | " | C₆H₅- | 83–84 | 71.81 / 71.29 | 7.09 / 7.03 | 9.85 / 10.52 |
| 34 | " | " | 4-Cl-3-CONH₂-C₆H₃- | 172–173.5 | 59.75 / 59.88 | 5.57 / 5.74 | 11.61 / 11.63 |
| 35 | 2-CH₃O— | 3-CH₃O— | 4-Cl-3-CONH₂-C₆H₃- | 170.5–172 | 58.24 / 57.67 | 5.66 / 5.72 | 10.72 / 10.46 |

EXAMPLE 36

To 5.0 g of 2-(3-carbamoylphenylamino)-N-(3,4-dimethoxyphenethyl)acetamide hydrochloride was added 500 ml of water heated at 55° to 60° C. and the mixture was stirred while heating at the same temperature until the hydrochloride completely dissolved. After allowing the mixture to stand overnight, the crystals precipitated were collected by filtration, washed with water and air-dried by allowing to stand at room temperature for 10 days to obtain 4.2 g of 2-(3-carbamoylphenylamino)-N-(3,4-dimethoxyphenethyl)acetamide trihydrate as colorless needles having a melting point of 53.5°–55.5° C.

The infrared absorption spectrum (KBr) of the trihydrate thus obtained showed absorption bands at around 3100–3600 cm$^{-1}$ assignable to the crystallized water.

Elemental Analysis for $C_{19}H_{29}O_7N_3$: Calcd.(%): C, 55.46; H, 7.10; N, 10.21. Found (%): C, 55.29; H, 7.15; N, 10.32.

Determination of the crystallized water by differential thermal analysis: Calcd. for $C_{19}H_{23}O_4N_3 \cdot 3H_2O$: $H_2O$, 13.1%. Found: $H_2O$, 13.0%.

EXAMPLE 37

A suspension of 1 g of 2-(3-carbamoylphenylamino)-N-(3,4-dimethoxyphenethyl)acetamide hydrochloride in 20 ml of water was vigorously stirred, whereupon the mixture became a viscous liquid at once and subsequently crystals were formed again. After stirring was continued for 30 minutes, the crystals were collected by filtration, washed with water and then air-dried by allowing to stand at room temperature for 10 days to obtain 0.88 g of 2-(3-carbamoylphenylamino)-N-(3,4-dimethoxyphenethyl)acetamide trihydrate as a crystalline powder having a melting point of 51°–56° C.

EXAMPLE 38

To 3.0 g of 2-(3-carbamoylphenylamino)-N-(3,4-dimethoxyphenethyl)acetamide hydrochloride were added 20 ml of 5% aqueous sodium carbonate solution and 125 ml of chloroform and then the mixture was stirred at room temperature until the hydrochloride completely dissolved. The chloroform layer was separated, washed with water, dried and the solvent was concentrated to dryness under reduced pressure. The residue was crystallized from a mixture of methanol and diethyl ether to obtain 2.3 g of 2-(3-carbamoylphenylamino)-N-(3,4-dimethoxyphenethyl)acetamide having a melting point of 133° to 135° C.

Elemental Analysis for $C_{19}H_{23}O_4N_3$: Calcd.(%): C, 63.85; H, 6.48; N, 11.76. Found (%): C, 63.59; H, 6.40; N, 11.71.

To 0.2 g of pulverized 2-(3-carbamoylphenylamino)-N-(3,4-dimethoxyphenethyl)acetamide was added 100 ml of water and the mixture was stirred at 60° to 65° C. for 30 minutes to dissolve the powder completely. The solution was then concentrated under reduced pressure at 60° C. until about 40 ml of residual liquid was left, and allowed to stand at room temperature overnight. The colorless needles precipitated were collected by filtration, washed with water and then air-dried by allowing to stand at room temperature to obtain 0.13 g of 2-(3-carbamoylphenylamino)-N-(3,4-dimethoxyphenethyl)acetamide trihydrate having a melting point of 54°–57° C.

EXAMPLE A

To a mixture of 0.34 g of 2-amino-4-chlorobenzamide, 0.57 g of monochloroacetic acid, 0.90 g of sodium iodide and 0.24 g of magnesium oxide was added 2 ml of dimethylformamide and the mixture was stirred at a temperature between 90° and 100° C. for 2.5 hours. After cooling, the reaction mixture was poured into 50 ml of a 2.6% aqueous sodium carbonate solution. The resulting precipitates were filtered off and the filtrate was extracted with 50 ml of chloroform. The aqueous layer was acidified with concentrated hydrochloric acid to precipitate crystals. The crystals were collected by filtration and recrystallized from aqueous methanol to obtain 0.20 g of N-(2-carbamoyl-5-chlorophenyl)glycine as needles having a melting point of 217°–222° C. (decomposition).

Elemental Analysis for $C_9H_9O_3N_2Cl$: Calcd.(%): C, 47.28; H, 3.97; N, 12.25. Found (%): C, 47.11; H, 3.74; N, 12.32.

EXAMPLE B

To a mixture of 6.8 g of 3-aminobenzamide, 5.5 g of methyl monochloroacetate and 10.0 g of calcium carbonate was added 30 ml of dimethylformamide and the mixture was stirred at 110° to 120° C. for 2 hours. The inorganic salt precipitated was filtered off and the filtrate was concentrated under reduced pressure. 50 ml of water was added to the resulting residue and the mixture was stirred to precipitate crystals. The crystals were collected by filtration, dried and recrystallized from a mixture of methanol and diethyl ether to obtain 5.7 g of N-(3-carbamoylphenyl)glycine methyl ester as colorless needles having a melting point of 146°–147° C.

Elemental Analysis for $C_{10}H_{12}O_3N_2$: Calcd.(%): C, 57.68; H, 5.81; N, 13.46. Found (%): C, 57.62; H, 5.71; N, 13.42.

To 4.2 g of N-(3-carbamoylphenyl)glycine methyl ester obtained above was added 50 ml of a 1 N aqueous sodium hydroxide solution and the mixture was stirred at room temperature for 30 minutes. The reaction solution was acidified with 4.2 ml of concentrated hydrochloric acid to precipitate crystals. The crystals were collected by filtration, washed with water, dried and then recrystallized from methanol to obtain 3.3 g of N-(3-carbamoylphenyl)glycine as colorless prisms having a melting point of 200°–222° C. (dec.).

Elemental Analysis for $C_9H_{10}O_3N_2$: Calcd.(%): C, 55.66; H, 5.19; N, 14.43. Found (%): C, 55.89; H, 5.30; N, 14.61.

While the invention has been described in detail and with reference to specific embodiments thereof, it will be apparent to one skilled in the art that various changes and modifications can be made therein without departing from the spirit and scope thereof.

What is claimed is:

1. N-phenethylacetamide compounds of the formula:

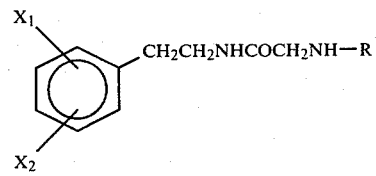

wherein $X_1$ represents a lower alkoxy group, $X_2$ represents a hydrogen atom or a lower alkoxy group and R represents a phenyl group, a pyridyl group or a pyrimidinyl group, each of which may have one or more substituents selected from a halogen atom, a carbamoyl group, a lower alkoxy group, a sulfamoyl group, an amino group, a lower alkylamino group, a lower alkylthio group, a hydroxy group and a lower alkoxycarbonyl group; or the pharmaceutically acceptable acid addition salts and hydrates thereof.

2. The compounds of claim 1, wherein said compounds are represented by the formula:

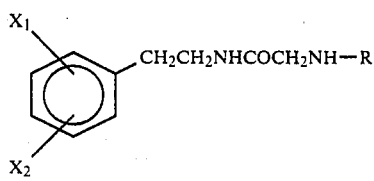

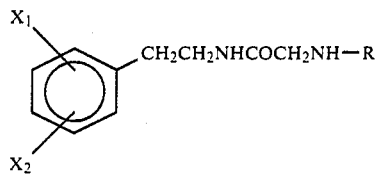

wherein $X_1$ and $X_2$ represent a lower alkoxy group, R represents a phenyl group or a carbamoylphenyl group, each of which may have one or more substituents selected from a halogen atom, a lower alkoxy group, a hydroxy group or an amino group, or the pharmaceutically acceptable acid addition salts and hydrates thereof.

3. The compound of claim 1, wherein said compound is crystalline 2-(3-carbamoylphenylamino)-N-(3,4-dimethoxyphenethyl)acetamide.3H$_2$O.

4. The compound of claim 1, wherein said compound is 2-(3-carbamoylphenylamino)-N-(3,4-dimethoxyphenethyl)acetamide or the pharmaceutically acceptable acid addition salt thereof.

5. The compound of claim 1, wherein said compound is 2-(2-carbamoyl-5-chlorophenylamino)-N-(3,4-dimethoxyphenethyl)acetamide or the pharmaceutically acceptable acid addition salt thereof.

6. A therapeutic agent for treating peptic ulcer comprising in an amount effective for treating pepetic ulcer at least one N-phenethylacetamide compound of the formula:

wherein $X_1$ represents a lower alkoxy group, $X_2$ represents a hydrogen atom or a lower alkoxy group, and R represents a phenyl group, a pyridyl group or a pyrimidinyl group, each of which may have one or more substituents selected from a halogen atom, a carbamoyl group, a lower alkoxy group, a sulfamoyl group, an amino group, a lower alkylamino group, a lower alkylthio group, a hydroxy group and a lower alkoxycarbonyl group; or the pharmaceutically acceptable acid addition salts and hydrates thereof, and a pharmaceutically acceptable carrier.

7. The therapeutic agent for treating peptic ulcer according to claim 6, wherein said compound is crystalline 2-(3-carbamoylphenylamino)-N-(3,4-dimethoxyphenethyl)acetamide.3H$_2$O.

8. The therapeutic agent for treating peptic ulcer according to claim 6, wherein said compound is 2-(3-carbamoylphenylamino)-N-(3,4-dimethoxyphenethyl)acetamide or the pharmaceutically acceptable acid addition salt or the hydrate thereof.

9. The therapeutic agent for treating peptic ulcer according to claim 6, wherein said compound is 2-(2-carbamoyl-5-chlorophenylamino)-N-(3,4-dimethoxyphenethyl)acetamide or the pharmaceutically acceptable acid addition salt thereof.

* * * * *